(12) United States Patent
Hiller

(10) Patent No.: US 10,512,502 B2
(45) Date of Patent: Dec. 24, 2019

(54) TISSUE SCISSORS FOR BIOLOGICAL TISSUE

(71) Applicant: ERBE Elektromedizin GmbH, Tübingen (DE)

(72) Inventor: Jürgen Hiller, Dettingen (DE)

(73) Assignee: Erbe Elektromedizin GmbH, Tübingen (DE)

(*) Notice: Subject to any disclaimer, the term of this patent is extended or adjusted under 35 U.S.C. 154(b) by 372 days.

(21) Appl. No.: 15/078,642

(22) Filed: Mar. 23, 2016

(65) Prior Publication Data
US 2016/0287320 A1    Oct. 6, 2016

(30) Foreign Application Priority Data

Mar. 30, 2015 (EP) .................................... 15161680

(51) Int. Cl.
*A61B 18/14* (2006.01)
*A61B 18/00* (2006.01)

(52) U.S. Cl.
CPC ...... *A61B 18/1447* (2013.01); *A61B 18/1445* (2013.01); *A61B 2018/0063* (2013.01);
(Continued)

(58) Field of Classification Search
CPC .... A61B 2018/00077; A61B 2018/146; A61B 2018/00083; A61B 2018/00095;
(Continued)

(56) References Cited

U.S. PATENT DOCUMENTS

| | | | |
|---|---|---|---|
| 5,484,436 A | 1/1996 | Eggers et al. | |
| 5,925,039 A * | 7/1999 | Landingham | A61B 18/14 606/41 |

(Continued)

FOREIGN PATENT DOCUMENTS

| | | | |
|---|---|---|---|
| DE | 4212053 C1 | 1/1996 | |
| EP | 0517244 A1 * | 12/1992 | ............. A61B 18/12 |

(Continued)

OTHER PUBLICATIONS

European Search Report in corresponding European Application No. 15161680, dated Sep. 30, 2015, 8 pages.
(Continued)

*Primary Examiner* — Thomas A Giuliani
*Assistant Examiner* — Christine A Dedoulis
(74) *Attorney, Agent, or Firm* — Fitch, Even, Tabin & Flannery LLP

(57) ABSTRACT

The invention relates to tissue scissors (10) with improved stability and improved handling that have two structurally and electrically different branches (11, 12). While the sliding surface (25) of the first branch (11) has a metal-ceramic hard material layer (30), such as, for example, titanium nitride, the second sliding surface (34) of the second branch (12) has an electrically non-conductive ceramic layer (33). The material mating produces great mechanical resistance to abrasion in the bearing (17) and on the cutting edges (28, 35). At least one of the branches, in particular branch (12), can have a cermet body (36) to improve the cooling of the cutting edge (35 (28)) and/or keep it sharp, to prevent heating of the branches (11, 12) during coagulation and sticking of the tissue.

11 Claims, 3 Drawing Sheets

(52) U.S. Cl.
CPC .............. *A61B 2018/00077* (2013.01); *A61B 2018/00083* (2013.01); *A61B 2018/00095* (2013.01); *A61B 2018/00607* (2013.01); *A61B 2018/146* (2013.01)

(58) Field of Classification Search
CPC .. A61B 2018/00607; A61B 2018/0063; A61B 18/1447; A61B 18/1445; A61B 17/32
USPC .......................................................... 606/50
See application file for complete search history.

(56) References Cited

U.S. PATENT DOCUMENTS

| | | | |
|---|---|---|---|
| 5,925,043 A | 7/1999 | Kumar et al. | |
| 6,106,542 A | 8/2000 | Toybin | |
| 6,312,430 B1* | 11/2001 | Wilson | A61B 18/1445 |
| | | | 606/50 |
| 6,447,511 B1 | 9/2002 | Slater | |
| 6,974,452 B1* | 12/2005 | Gille | A61B 18/1402 |
| | | | 606/37 |
| 2002/0019632 A1* | 2/2002 | Mayenberger | A61B 18/1445 |
| | | | 606/48 |
| 2003/0199869 A1* | 10/2003 | Johnson | A61B 18/1445 |
| | | | 606/50 |
| 2007/0213712 A1* | 9/2007 | Buysse | A61B 18/1442 |
| | | | 606/51 |
| 2013/0035685 A1 | 2/2013 | Fischer et al. | |
| 2013/0338663 A1 | 12/2013 | Cao et al. | |

FOREIGN PATENT DOCUMENTS

| | | |
|---|---|---|
| EP | 2554132 A1 | 2/2013 |
| JP | 2000512521 A | 9/2000 |
| RU | 2003114764 A | 2/2005 |

OTHER PUBLICATIONS

European Patent Office Examination Report dated Apr. 13, 2018 for European Patent Application No. 15161680.2 (8 pages).
Russian Office Action dated Apr. 22, 2019, in corresponding Russian Patent Application No. 2016111733/14 (018525), with English translation (12 pages).
Japanese Office Action dated Jul. 9, 2019, in corresponding Japanese Patent Application No. 2016-069453, with English translation (7 pages).
Chinese Second Office Action dated Aug. 23, 2019, in corresponding Chinese Application No. 201610182481.1, with English translation (15 pages).

* cited by examiner

TISSUE SCISSORS FOR BIOLOGICAL TISSUE

RELATED APPLICATION(S)

This application claims the benefit of European Patent Application No. EP 15161680.2 filed Mar. 30, 2015, the contents of which are incorporated herein by reference as if fully rewritten herein.

TECHNICAL FIELD

The invention relates to tissue scissors for cutting biological tissue while simultaneously sealing the resulting tissue edges by denaturation of the proteins.

BACKGROUND

U.S. Pat. No. 5,925,039 discloses an electrosurgical instrument in the form of a scalpel or scissors, wherein an active electrode surface consists of an electrically conductive hard metal, such as, for example, tungsten carbide. This can be applied in a layer on an electrically conductive or non-conductive support. The hard metal surface's better heat conduction means that it exhibits less tissue adhesion than surfaces made of stainless steel.

US 2013/0338663 A1 discloses an ablation catheter whose ablation electrode is in thermal contact with a heat sink, but which is electrically insulated from the ablation electrode. The heat sink can consist of diamond-like carbon (DLC), aluminum nitride, a thermally conductive synthetic resin, i.e., a ceramic, or other nonconductors.

U.S. Pat. No. 5,925,043 proposes an electrosurgical electrode with a conductive non-stick coating. This is done by providing a metal electrode with a hard material layer (titanium nitride) that is considered to be a ceramic layer. In addition, other ceramic layers (transition metal nitrides) are proposed.

DE 42 12 053 C1 also discloses forceps whose branches have, at their ends, a layer made of (going from inside to outside) a corrosion protection layer, a hard material layer, and a precious metal layer.

SUMMARY

It is the goal of the invention to specify tissue scissors for cutting biological tissue whose use leaves the edges of the cut clean and well-sealed while being quite gentle with the surrounding tissue.

The inventive tissue scissors have two branches whose facing sliding surfaces have different layers on them. While the first branch preferably has, on its cutting surface, an electrically conductive hard material layer (that is a cermet layer), the second branch has an electrically insulating ceramic layer. Since one of the two sliding surfaces is not electrically conductive, but the other one is conductive, this produces electrical asymmetry. Coating the one branch with an electrically non-conductive ceramic produces a largely current-free area near the coated surface of this branch and concentrates the current near the associated cutting edge. In addition, the energy flow is guided through the coating. This means that when biological tissue is cut, the energy, i.e., the current, flows from the cutting surface of the first branch through the back of the second branch to the neutral electrode.

The desired physiological effect is supported by effective cooling of the branch that has the insulating ceramic layer. Here the heat distribution and heat dissipation are achieved by a hard metal body (which is also referred to as a cermet body). The cermet body can consist, e.g., of tungsten carbide or another suitable sintered metal carbide and a binder like cobalt, nickel or molybdenum. The cermet body, which is preferably put on only one of the branches, results in thermal asymmetry. This can be used to compensate for the thermal resistance inherent in the ceramic layer.

Preferably, the cermet body on the back surface of the branch is bare (no coating), so that the cermet body there can dissipate the heat absorbed near the cutting edge and on the ceramic layer in a distributed manner, without affecting the coagulation functionality.

The cermet body is in contact with the ceramic layer, especially in the vicinity of the cutting edge. Preferably, the cermet body extends over the entire length of the cutting edge. At least at some places of the branch, the cermet body may also extend over the entire width of the ceramic layer, measured at right angles to the cutting edge. Preferably it does so along the entire cutting edge.

The thermal contact between the sliding surface or the ceramic layer located on it and the cermet body forms a cooling zone in which the cut and coagulated edge of the biological tissue is cooled, so that uncontrolled progression of the coagulation is avoided. In addition, the improved heat dissipation reduces, or preferably avoids, adhesion of the tissue to the branch.

Embodiments are also possible in which the branch provided with the hard material (cermet) layer (e.g., titanium nitride) comprises a cermet body, to have an effect on heat management here.

Typically, the first branch consists of steel, while the second branch consists of a combination of the cermet body and a steel support. The cermet body and the steel support can be connected with one another through a seam that can be in the form of a soldered seam or a weld seam. This produces a gapless connection between the support and the cermet body. Both branches may comprise a cermet body as described above.

It is preferable for both, the cermet layer (that is the hard material layer) and/or the ceramic layer, to extend through the joint over the entire length of the respective branch. The electrically nonconductive ceramic layer supports the electrical insulation of the branches from one another. Moreover, both the hard material layer and the ceramic layer substantially contribute to minimizing the wear of the joint connection and thus to the precise guidance of the branches, so that even after long use and operation and after being sterilized many times a clean cut on the tissue is always achieved. The selection of different materials for the hard material layer and the ceramic layer makes it possible to create a friction pairing with low friction and high stability. This can make the tissue scissors especially easy to operate and durable.

Further details about advantageous embodiments of the invention follow from the claims, the drawing, or the description. The figures are as follows:

DETAILED DESCRIPTION

Figure 1:
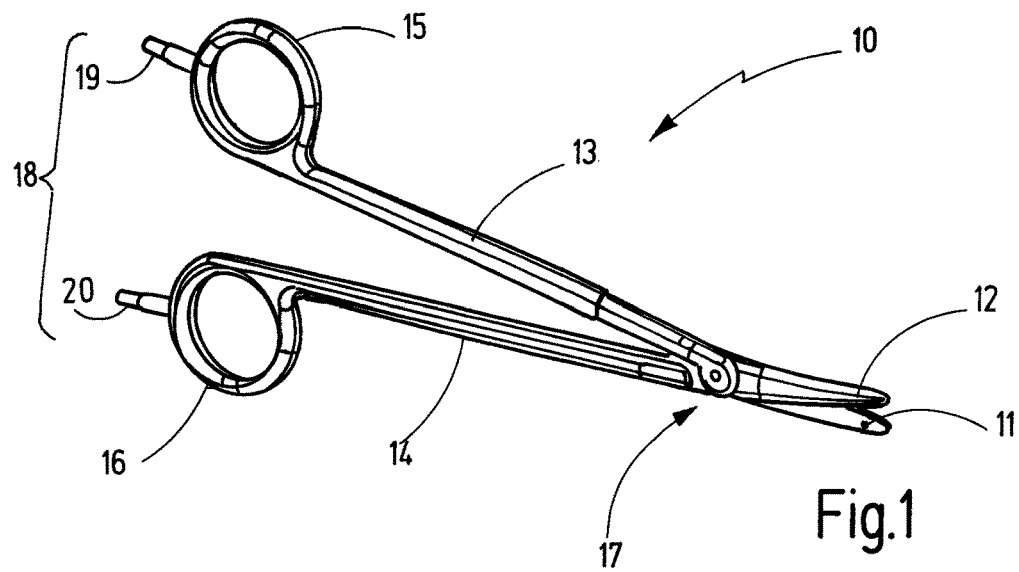
FIG. 1 is a first perspective view of the inventive tissue scissors.

FIG. 1 illustrates tissue scissors 10 that are used to cut biological tissue and, if desired, to seal the resulting tissue margins by coagulation or cauterization. The tissue scissors 10 has a first branch 11 and a second branch 12, each of which changes into respective handles 13, 14, which can have eye rings 15, 16 or other means of manipulation at their ends. The branches 11, 12 are held against one another at a joint 17 so that they can pivot and so that the handles 13, 14 can pivot toward one another and away from one another.

Figure 2:
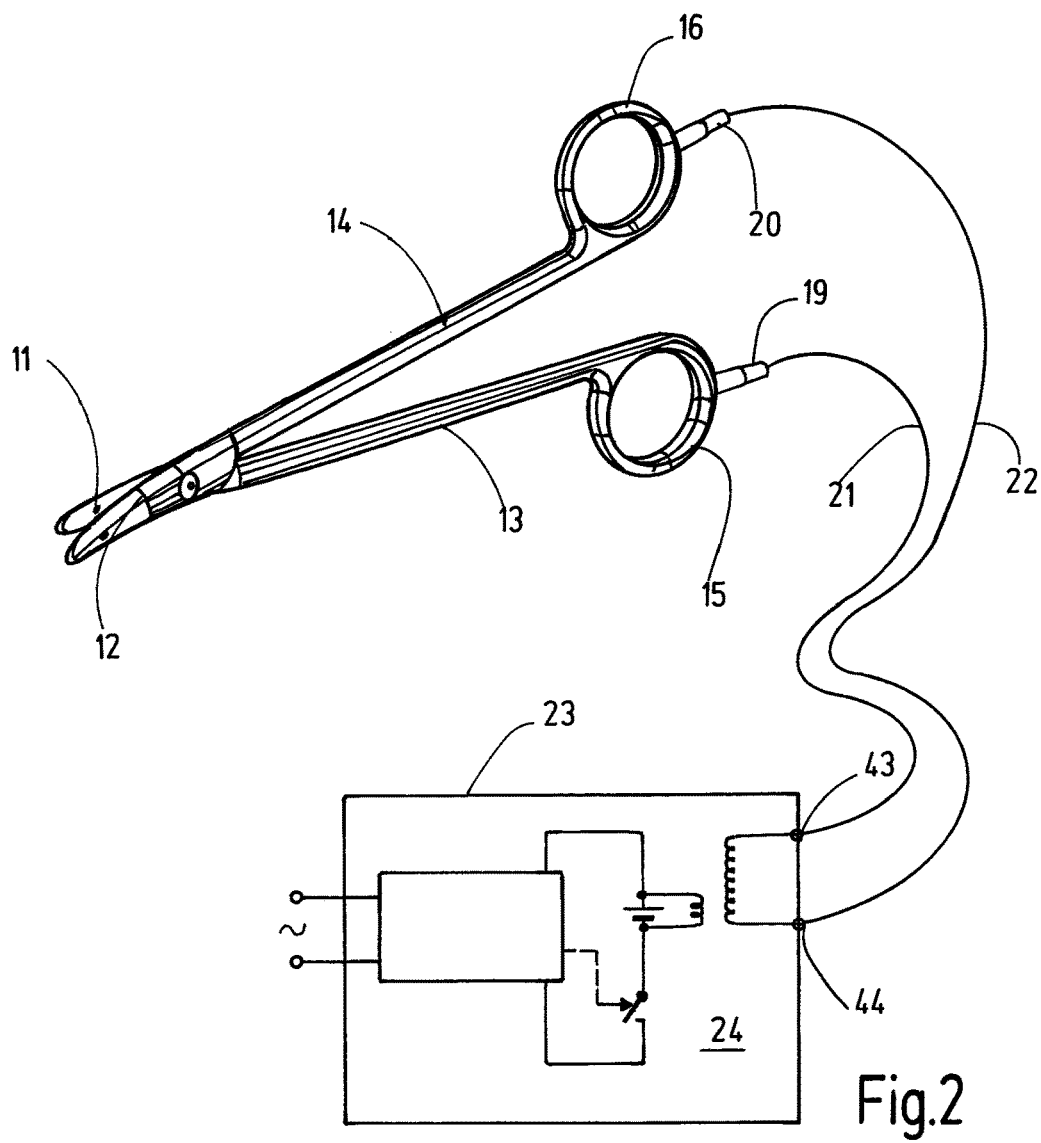
FIG. 2 is a second perspective view of the inventive tissue scissors shown in FIG. 1 and a schematic diagram of a device that supplies power to them.

The tissue scissors 10 are provided with an electrical connection 18 that has one double or two single plug contact means 19, 20, which is/are arranged on one or both of the eye rings 15, 16. The plug contact means are preferably contact pins, to which the wires 21, 22 can be connected, as is schematically shown in FIG. 2, and which serve for connection to an electrical device 23 that supplies power through a first terminal 43 and a second terminal 44.

The electrical device 23 contains a HF generator 24 that supplies high-frequency electrical voltage (preferably between 200 kHz and 4 MHz) to the branches 11, 12 to bring about HF coagulation of the biological tissue. Means of operation are present to turn the generator 24 on and off in a controlled manner, however are not separately illustrated in FIG. 2.

Figure 3:
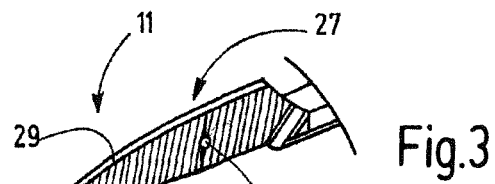
FIG. 3 shows a branch of the tissue scissors shown in FIGS. 1 and 2.

FIG. 3 separately illustrates the first branch 11. It has a sliding surface 25, that is essentially flat and that extends beyond the joint area 27 marked by a drill hole 26. It is preferable if the sliding surface 25 is essentially flat and extends all the way to the distal end of the branch 11. The sliding surface 25 abuts a cutting edge 28 of the branch 11, and extends all the way to the opposite edge 29. The sliding surface 25 can be continuous, as shown, and have a hard material layer 30. The hard material layer 30 at least abuts the cutting edge 28, and can continuously extend beyond that over the entire sliding surface 25. In particular, the hard material layer 30 can extend all the way to the edge 29. The edge 29 is arranged opposite the cutting edge 28. In addition, the hard material layer 30 can occupy parts of the other surface of the branch 11.

The hard material layer 30 is preferably an electrically conductive layer, such as, for example, a titanium nitride layer or another layer, especially an electrically conductive hard material layer (titanium carbide, titanium carbonitride, etc.).

Figure 4:
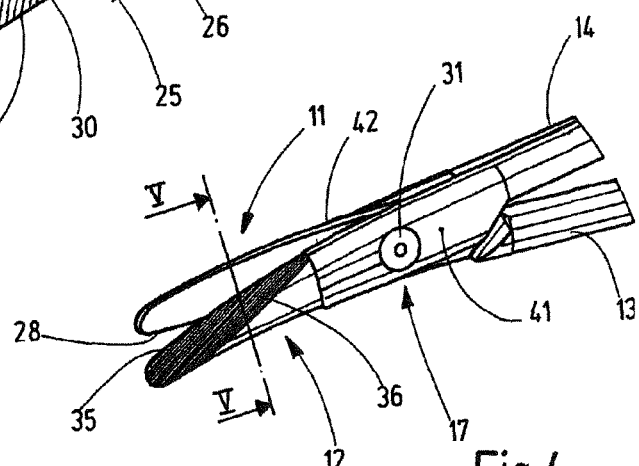
FIG. 4 is a perspective view of a detail of the tissue scissors shown in FIG. 2.

FIG. 4 illustrates the branch 11 in connection with the branch 12, which are pivotably connected with one another at the joint 17 by a rivet 31, a screw, or means of connection of that kind. The means of connection have insulation on the outside. This avoids an unwanted current flow. The second branch 12 has, on its sliding surface 34 facing the first branch 11, a ceramic layer 33 (FIG. 5) that chemically and/or structurally differs from the hard material layer 30. The ceramic layer 33 forms a sliding surface 34 that extends all the way to the distal end of the second branch 12. The ceramic layer 33, and thus the sliding surface 34, also extends from the cutting edge 35 of the second branch 12 all the way to the opposite edge 45, which runs in the longitudinal direction of the branch 12. The preferably flat sliding surface 34 preferably extends from the distal end of the branch 12 all the way to the joint 17 and beyond it. Preferably, the ceramic layer 33 is continuous over its entire surface, so that the branch 12, which otherwise consists of metal, has no electrical contact with the branch 11; in other words, branch 12 is electrically insulated from branch 11. To accomplish this, in addition the rivet 31 can be made of plastic, ceramic, or of metal covered with an insulating material.

Figure 5:
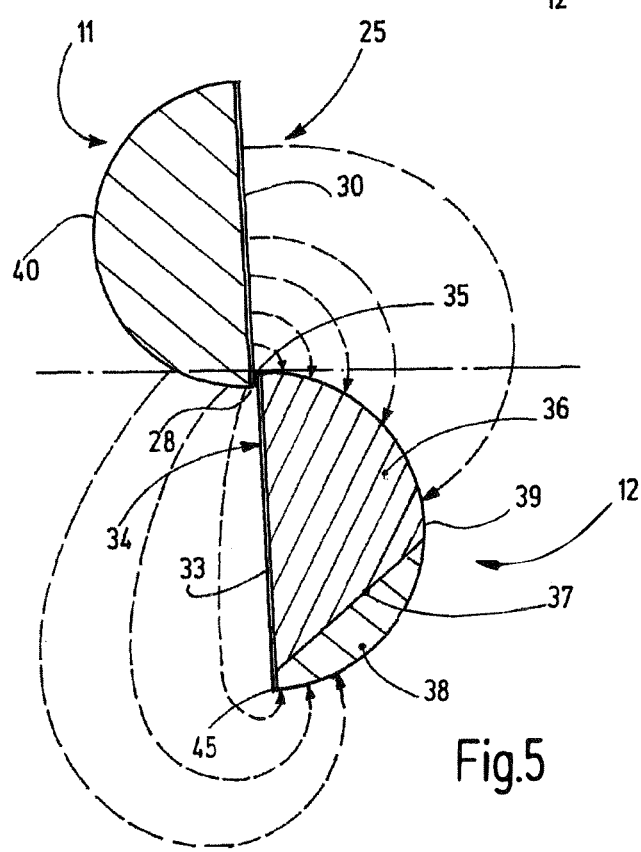
FIG. 5 is a cross-section along the line V-V of the tissue scissors shown in FIG. 4; this simplified representation omits the joint and handle, and shows the current flow that is produced during operation.

As is suggested in FIG. 5, the branch 11 consists of a uniform material, e.g., steel, which supports the hard material layer 30 on the sliding surface 25. By contrast, the branch 12 has a cermet body 36 that extends over a considerable part of the second branch 12 along its length (see FIG. 4). It is preferable if the cermet body 36 at the distal end of the branch 12 extends from the cutting edge 35 all the way to the lower opposite edge 45. In the direction toward the joint 17, the cross section of the cermet body 36 that is shown separately in FIG. 5 can decrease in surface area. The length of the cermet body 36 is preferably greater than half the distance of the distal end of the branch 12 from the joint 17. The cermet body 36 can, as shown in FIG. 5, be connected with a support structure 38 of the branch 12 at a seam 37. The support structure 38 consists, e.g., of steel and tapers, starting from the full cross section of the branch 12 to zero at the distal end. The support structure 38 ends before reaching the distal end of the branch 12. The seam 37 can be a soldered seam, a weld seam, or a material connection of that kind. On the back 39 of the branch 12 facing away from the sliding surface 34, both the cermet body 36 and the support structure 38 are exposed. The same goes for the branch 11. There the back 40 facing away from the sliding surface 25 is also exposed.

As can be seen in FIG. 4, the handles 13, 14 have an electrically insulating layer 41, 42 that preferably extends all the way to the branches 11, 12, but leaves them exposed on the sliding surfaces 25, 34 and areas the backs 39, 40. The covering of the branches 11, 12 by the insulating layer 41, 42 can depend on the purpose. It is possible for almost the entire back 39, 40 to be covered by the insulating layer 41, 42 and for the branches to lack the insulating layer only in the area of the distal end.

Figure 6:
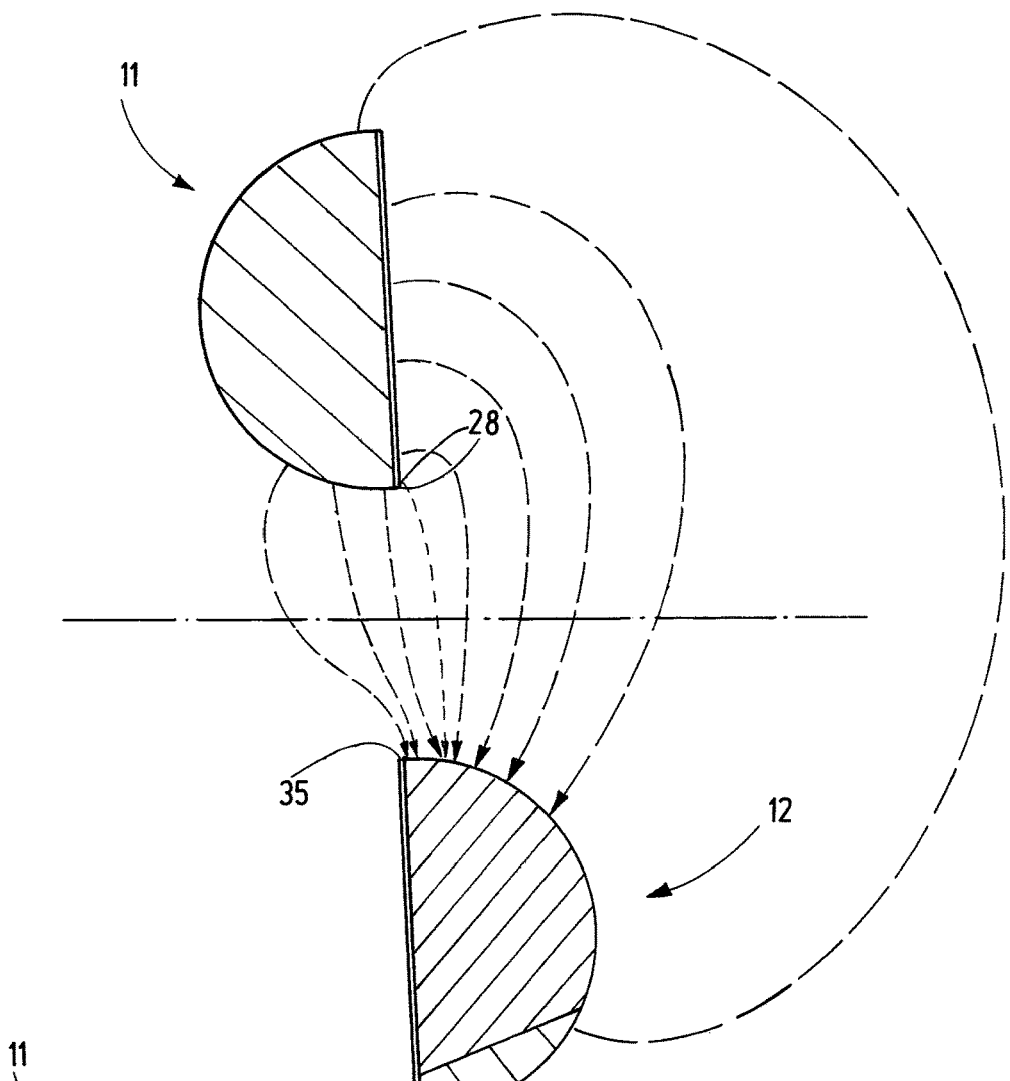
FIG. 6 is a cross section of the branches similar to FIG. 4 [sic] before the cut, along with the current flow that is produced during operation.
Figure 7:
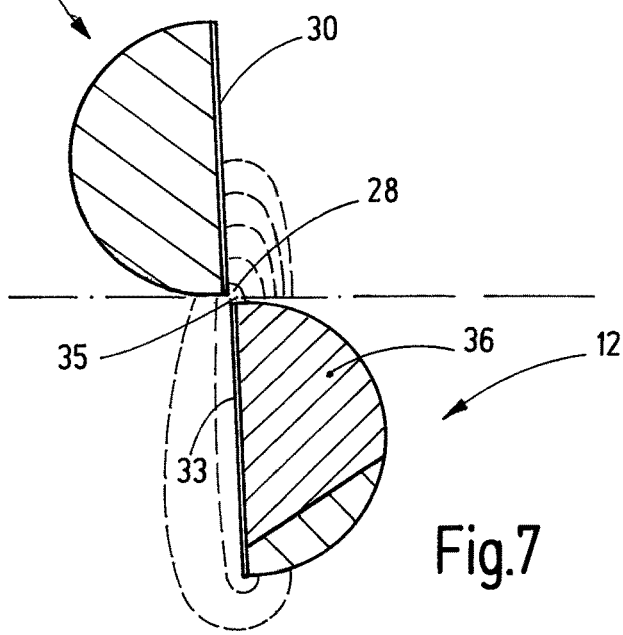
FIG. 7 is a representation similar to FIGS. 5 and 6 of the tissue scissors in FIG. 4 at the cutting point.

The tissue scissors 10 described in this respect work as follows:

FIGS. 5, 6, and 7 illustrate cross sections of the branches 11, 12 along the line V-V in FIG. 4, shown in various stages of closure.

FIG. 5 shows the branches 11, 12 after they have taken hold of biological tissue (not shown), and are applying mechanical pressure to it before cutting it. If the generator 24 is now simultaneously activated, it produces a flow, through the tissue, of high-frequency electrical current whose current lines are shown as dashed lines in FIG. 6. The current density increases as the cut progresses, as illustrated in FIG. 7. The electrically insulating effect of the ceramic layer 33 avoids an electrical short circuit at the cutting edges 28, 35. However, in the immediate vicinity of the cutting edges 28, 35, there is a high current density that heats and coagulates the tissue. The proteins denaturing in the resulting heat have the potential to stick. If they would adhere or stick to the branches 11, 12, this would hinder the work, and in the worst case interrupt the current flow. As a consequence, the coagulation effect of the tissue scissors would no longer be present or would be very strongly limited, which in turn would lead to a qualitatively poor result. Soiling of a branch by denatured protein has a massive influence on the coagulation function of the tissue scissors. Since the user might not notice this effect immediately, he might continue to cut the tissue (the cutting function is not affected) without the vessels being successfully sealed as he does so. Therefore, this can result in bleeding. The cermet body 36, whose thermal conductivity is higher than that of steel, counteracts tissue adhesion. The cermet body 36 effectively cools the branch 12, which is made of steel, and its ceramic layer 33. This, in connection with the adhesion-reducing hard material layer 30, which is cooled by this layer itself and possibly by the branch, produces an improved cutting or coagulation result. In particular, the conditions can be adjusted so that the cooling effect of the hard material layer 30 in connection with the steel branch 11 is comparable with the cooling effect of the combination of the ceramic layer 33 and the cermet body 36. The small thermal conductivity of the ceramic layer 33 is balanced by the high thermal conductivity of the cermet body 36.

The continued cut produces a flow of electricity such as that pictured in FIG. 5. Although the branches 11, 12 are structurally and electrically asymmetric, the areas of the backs 39, 40 close to the cutting edge have a comparable electrical flow through them, and thus a comparable coagulation effect.

Tissue scissors 10 with improved stability and improved handling have two structurally and electrically different branches 11, 12. While the first branch 11 has, on its sliding surface 25 a metal-ceramic hard material layer 30, such as, for example, titanium nitride, the second sliding surface 34 of the second branch 12 has an electrically non-conductive ceramic layer 33. The material mating produces great mechanical resistance to abrasion in the bearing 17 and on the cutting edges 28, 35. At least one of the branches, in particular branch 12, can have a cermet body 36 to improve the cooling of the cutting edge 35 (28) and/or keep it sharp, to prevent heating of the branches 11, 12 during coagulation and sticking of the tissue.

REFERENCE NUMBERS

| 10 | Tissue scissors |
| 11 | First branch |
| 12 | Second branch |
| 13, 14 | Handle |
| 15, 16 | Eye ring |
| 17 | Joint |
| 18 | Electrical connection |
| 19, 20 | Plug contact means |
| 21, 22 | Wires |
| 23 | Device |
| 24 | Generator |
| 25 | First sliding surface |
| 26 | Drill hole |
| 27 | Joint area |
| 28 | Cutting edge of the first branch 11 |
| 29 | Edge opposite the cutting edge 28 |
| 30 | Hard material layer/cermet layer |
| 31 | Rivet |
| 33 | Ceramic layer |
| 34 | Second sliding surface |
| 35 | Cutting edge of the second branch 12 |
| 36 | Cermet body |
| 37 | Seam |
| 38 | Support structure |
| 39, 40 | Backs |
| 41, 42 | Insulating layer |
| 43, 44 | First terminal, second terminal |
| 45 | Edge opposite cutting edge 35 |

What is claimed is:

1. Tissue scissors (10) to cut biological tissue, the tissue scissors comprising:
   a first branch (11) that has a first sliding surface (25), which ends at a first cutting edge (28);
   a second branch (12) that has a second sliding surface (34), which ends at a second cutting edge (35); and
   a joint (17) at which the first branch and the second branch are pivotably connected, so that the first sliding surface and the second sliding surface face one another and the first cutting edge (28) can be moved past the second cutting edge (35);
   wherein the first branch is formed from a steel material and the first sliding surface (25) includes an electrically conductive hard material layer (30) different from the steel material;
   the second sliding surface (34) includes an electrically non-conductive ceramic layer different from the hard material layer of the first sliding surface (25);
   wherein the second branch has a distal end and a length measured from the joint to the distal end and is formed at least in part by a cermet body (36) which has a length greater than half of the length of the second branch, which extends along an entire length of the second cutting edge, and which forms a surface facing the first sliding surface upon which at least a portion of the ceramic layer of the second sliding surface (34) is directly formed such that the ceramic layer directly contacts the cermet body along the entire length of the second cutting edge, the second branch having an uncoated back surface facing away from the second sliding surface formed by the cermet body,
   wherein the cermet body has a thermal conductivity higher than a thermal conductivity of the steel material of the first branch and is configured to dissipate heat absorbed near the second cutting edge and by the electrically non-conductive ceramic layer;
   wherein the cermet body (36) is connected with a support (38) made of steel;
   wherein the cermet body (36) and the support (38) are connected with one another through a seam; and
   wherein the ceramic layer (33) covers the seam (37).

2. The tissue scissors described in claim 1, wherein the cermet body (36) is in heat exchanging contact with the second sliding surface (34) and the cermet body is exposed on a portion of the second branch (12) facing away from the second sliding surface (34).

3. The tissue scissors described in claim 1, wherein the second sliding surface (34) is disposed to be in thermal contact with the cermet body (36).

4. The tissue scissors described in claim 1, wherein the cermet body (36) is formed from a sintered metal carbide material.

5. The tissue scissors described claim 1, wherein the seam (37) is a soldered seam or a weld seam.

6. The tissue scissors described in claim 1, wherein the seam (37) extends in a direction away from the joint (17).

7. The tissue scissors described in claim 1, wherein the first sliding surface (25) and the hard material layer (30) extend through the joint (17).

8. The tissue scissors described in claim 1, wherein the second sliding surface (34) and the ceramic layer (33) extend through the joint (17).

9. The tissue scissors described in claim 1, wherein the first branch (11) and the second branch (12) are each connected with a respective handle (13, 14).

10. The tissue scissors described in claim 9, wherein the respective handles (13, 14) have respective layers of electrical insulation (41, 42).

11. The tissue scissors described in claim 1, wherein the first branch (11) is disposed to allow connection with a first terminal (43) of an electrical device (24) and the second branch (12) is disposed to allow connection with a second terminal (44) of the electrical device (24).

* * * * *